United States Patent [19]

Melton

[11] Patent Number: 4,515,896

[45] Date of Patent: May 7, 1985

[54] FLUORESCENT ADDITIVES FOR THE DETERMINATION OF CONDENSED AND VAPOR PHASES IN MULTIPHASE SYSTEMS

[75] Inventor: Lynn A. Melton, Richardson, Tex.

[73] Assignee: United Technologies Corporation, Hartford, Conn.

[21] Appl. No.: 560,729

[22] Filed: Dec. 12, 1983

[51] Int. Cl.[3] ............... G01N 21/63; G01N 21/64
[52] U.S. Cl. .................... 436/2; 73/861.04; 250/356.1; 356/417; 436/35; 436/172; 436/905
[58] Field of Search ............ 436/139, 60, 2, 905, 436/172, 35, 56; 250/461.1, 328, 458.1, 356.1; 356/317, 318, 417; 73/861.04, 861.07, 861.39

[56] References Cited

U.S. PATENT DOCUMENTS

| | | | |
|---|---|---|---|
| 3,494,871 | 2/1970 | Clapp et al. | 436/56 X |
| 3,711,707 | 1/1973 | Lilienfeld et al. | 250/356.1 |
| 4,228,353 | 10/1980 | Johnson | 73/861.04 X |
| 4,282,433 | 8/1981 | Löffel | 250/356.1 |
| 4,350,661 | 9/1982 | Davis et al. | 436/2 X |

OTHER PUBLICATIONS

Khutoryanskii et al., Colloid J. of the USSR, vol. 36, No. 4, pp. 756–759 (1/1975).
Peterson et al., Rev. Sci. Instrum. vol. 51, No. 5 (May 1980), pp. 670–671.

Primary Examiner—Arnold Turk
Assistant Examiner—Robert Hill, Jr.
Attorney, Agent, or Firm—Alan C. Cohen

[57] ABSTRACT

A method for determining the spatial and phase distribution of a liquid-vapor multiphase fluid. The method comprises adding a fluorescent monomer and a quencher to the fluid to be studied. The fluid is then dispersed and the monomer excited. The excited monomer combines with the quencher to form a fluorescent exciplex. The monomer fluorescence is predominantly in the vapor phase and the exciplex fluorescence is predominantly in the liquid phase.

4 Claims, 6 Drawing Figures

FLUORESCENT ADDITIVES FOR THE DETERMINATION OF CONDENSED AND VAPOR PHASES IN MULTIPHASE SYSTEMS

DESCRIPTION

1. Technical Field

The field of art to which this invention pertains is testing methods and specifically methods of determining spatial and phase distribution of liquid-vapor multiphase systems.

2. Background Art

In liquid fueled combustors, the fuel is converted to a spray consisting of a system of fuel droplets, and fuel vapor. Such fuel sprays contain numerous individual droplets which can range in size from about 2 to about 200 μm. These droplets must evaporate, and mix with the oxidant, which is generally air, before effective combustion can occur. In attempting to better understand the events which are occurring within these combustors, literally hundreds of theoretical and experimental investigations have been performed concerning a single, isolated droplet as well as the complex, multi-droplet sprays.

The optical measurement of the separate vapor and liquid phases of the fuel spray is made difficult because of the paucity of spectroscopic characteristics which differ significantly for organic (fuel) molecules in the two phases. Spontaneous Raman scattering investigation concluded that, in the C-H stretching region near 3000 cm$^{-1}$, there were insufficient differences between the spectra of the vapor and liquid to allow their separate measurement. Other methods have exploited the index of refraction differences between the liquid droplets and the less dense ambient vapor/air surrounding the droplets and have used either direct photography, laser light scattering, or two-wavelength laser absorption/scattering. To date, virtually all spray investigations have inferred the amount of fuel in the vapor phase from complex measurements of the distribution of droplet sizes; these techniques require considerable data collection and analysis time so that usually only the averaged behavior of the fuel spray can be determined.

It is clear that there is a need for an improved understanding of the dominant physical and chemical processes associated with the combustion of droplet sprays. Ideally, this understanding would follow from studying the combustion process, in situ, under dynamic combustion activity. To date, there have been a number of techniques proposed, as mentioned above. However, none of these allow for a continuous, dynamic, two-dimensional, in situ study of both the liquid and vapor phases simultaneously.

Therefore, what is needed in the art is an improved method for determining the spatial and phase distribution of a liquid-vapor multiphase system which will allow for an in situ, dynamic, multi-dimensional characterization of fuel droplets in a combustion.

DISCLOSURE OF INVENTION

The present invention discloses a method for determining the spatial and phase distribution of a liquid-vapor multiphase system. The method comprises adding an exciplex system of at least two components to the fluid material to be studied. One of the components is a fluorescent monomer which, when excited, combines with the other component, the quencher, to form a fluorescent exciplex which fluoresces at a different wavelength than the fluorescent monomer. The system is designed such that the monomer fluorescence is dominant in the vapor phase and the exciplex fluorescence is dominant in the liquid phase. The two emissions are typically about 50 nm apart or greater. The spatial and phase distribution of the liquid-vapor system is determined by detecting the relative fluorescences emitted by the monomer and the exciplex.

Other features and advantages will be apparent from the specification and claims and from the accompanying drawings which illustrate an embodiment of the invention.

BEST MODE FOR CARRYING OUT THE INVENTION

Figure 1:
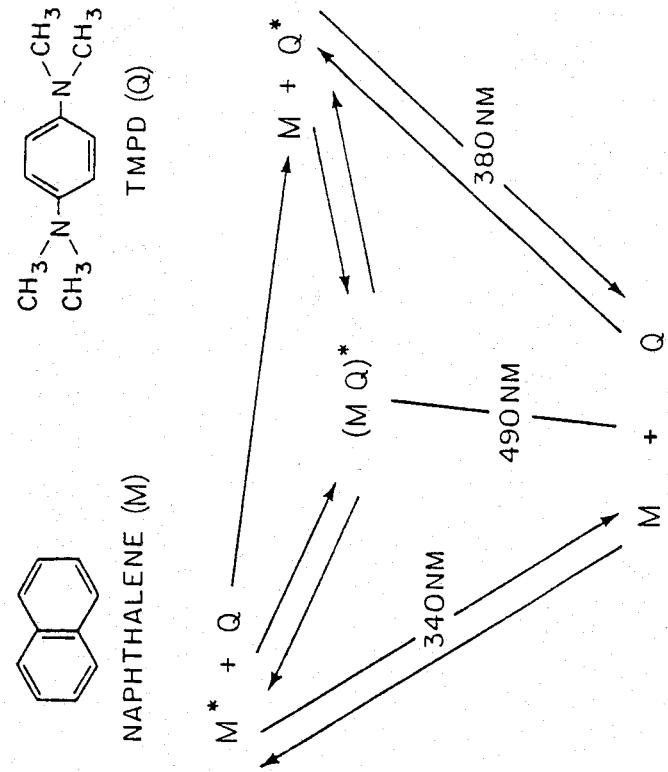
FIG. 1 is a schematic of the photophysics of a typical exciplex system.
Figure 2:
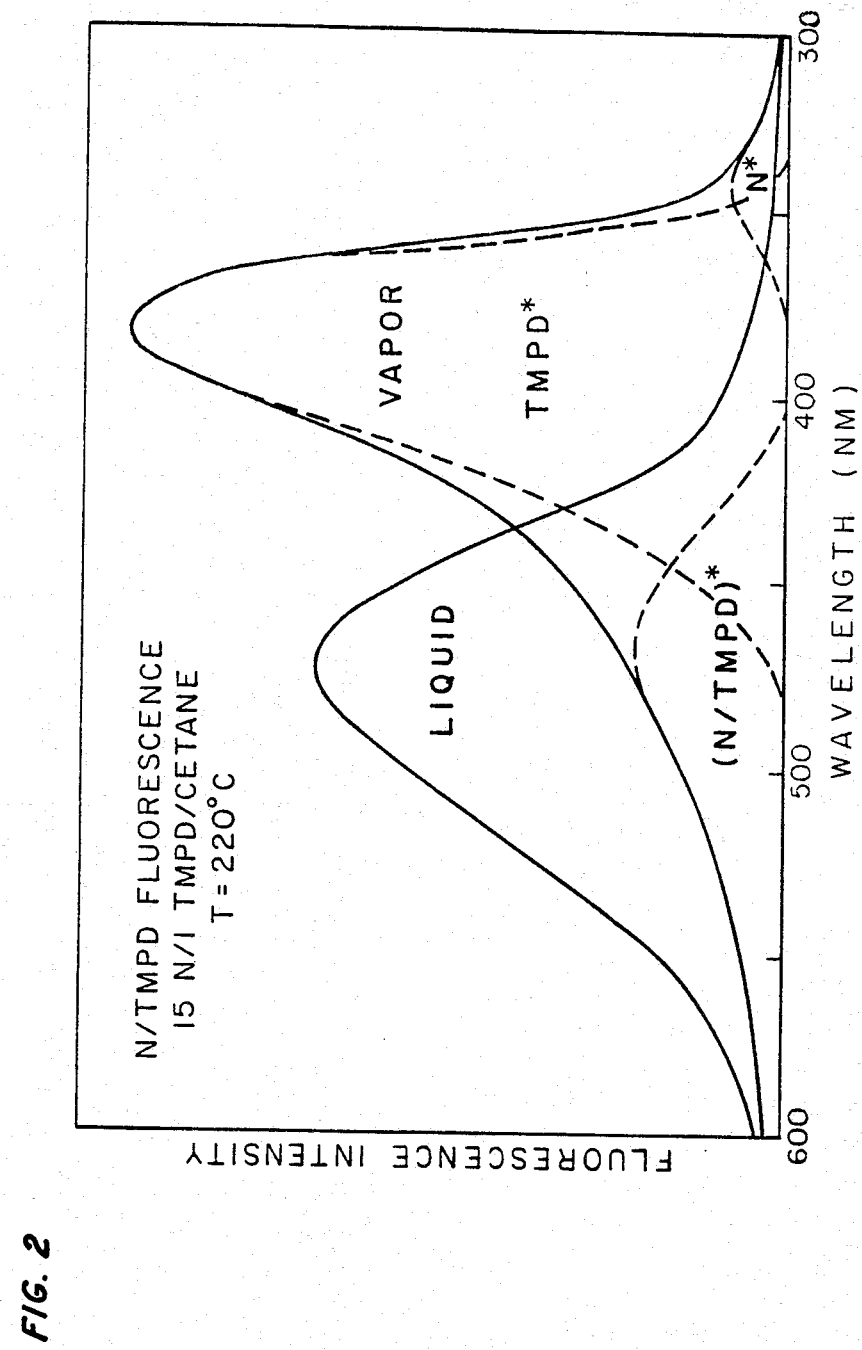
FIG. 2 is a graph depicting the fluorescence spectra of the liquid and vapor phases of 10% naphthalene, 1% tetramethyl-p-phenylene diamine (TMPD), 89% cetane at 220° C.
Figure 3:
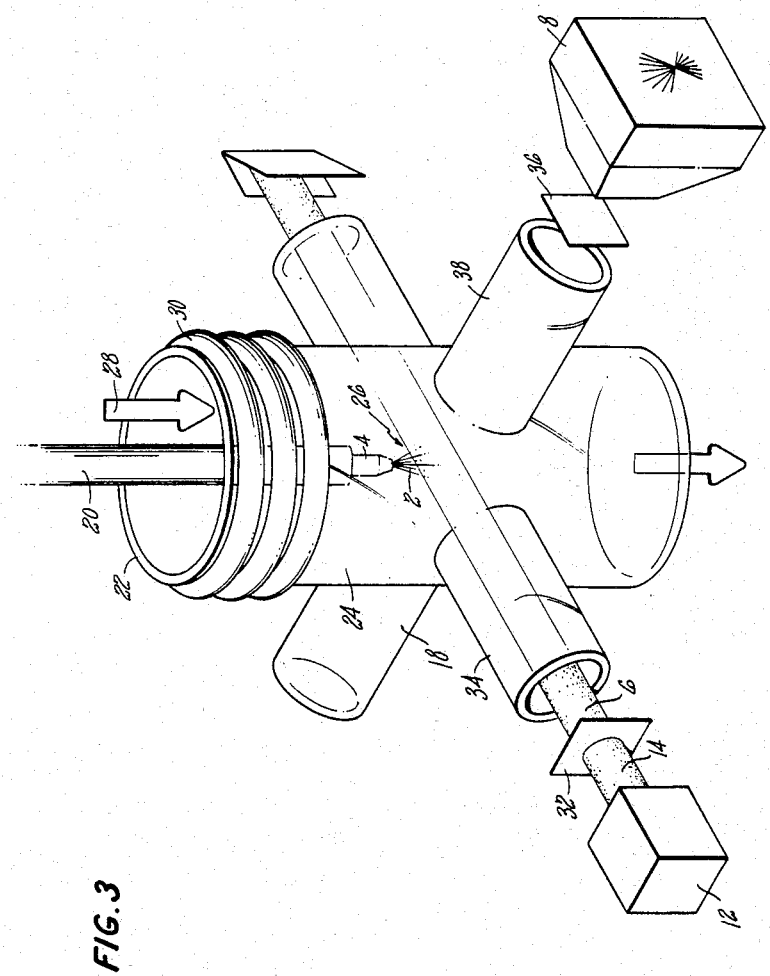
FIG. 3 is a schematic of a fuel spray visualization system.
Figure 6:
FIG. 6 is a photograph of the spatial distribution of the vapor phase of the synthetic fuel.
Figure 5:
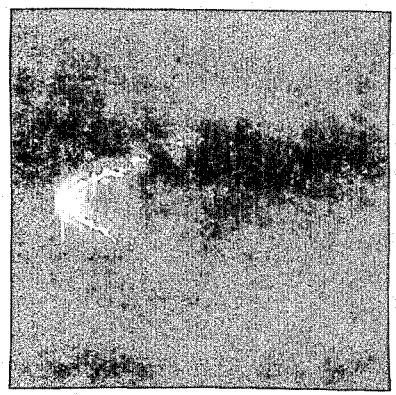
FIG. 5 is a photograph of the spatial distribution of the liquid phase of the synthetic fuel.
Figure 4:
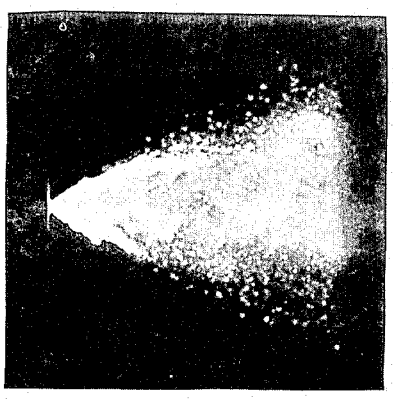
FIG. 4 is a photograph of the spatial and phase distribution of liquid and vapor of a synthetic fuel.

The exciplex system typically is comprised of a fluorescent monomer M, a quencher molecule Q and an exciplex MQ* formed by the collision of an excited M (M*) molecule and Q molecule. (If M is the same as Q, the resulting exciplex is also called an excimer.) M is typically an unsaturated, olefinic or aromatic molecule which can absorb light to form an electronically excited molecule M*. This excited molecule, M*, should have an average lifetime of about 10 to about 100 nanoseconds, during which time it may return to the ground state (M) by emitting light (fluorescence) at a particular wavelength or by combining with Q to form an exciplex MQ*. MQ* may itself return to the ground state by fluorescing at its own wavelength which typically differs from M by about 50 nm. M should also be chemically stable, volatile and soluble in the fluid material under study. A number of candidate materials are listed, along with some of their physical characteristics in Table I. Others will be known to those skilled in the art. It should be noted that the singlet excitation energy cited in the Tables is the energy required in electron volts/molecule to excite the molecule to the energy state at which state it will fluoresce or form the exciplex.

TABLE I

| Molecule | Normal Boiling Point (°C.) | Singlet Excitation Energy (eV/molecule) |
|---|---|---|
| naphthalene | 218 | 3.95 |
| tetramethyl-p-phenylene diamine | 260 | 3.41 |
| 1,2,4, trimethyl benzene | 168 | 4.34 |
| anthracene | 340 | 3.22 |
| phenanthrene | 336 | 3.57 |

Q may be the same molecule as M or it may be any number of organic molecules which possess the appropriate electron acceptor and/or donor characteristics to form a fluorescent emitting exciplex with M*, which will be stable at spray-evaporation temperatures or dispersion conditions. Additionally, Q should be chemically stable and soluble in the fluid material to be studied. A number of candidate materials which should be useful as Q are listed in Table II. Other materials useful as Q will be known to those skilled in the art.

TABLE II

| Molecule | Normal Boiling Point (°C.) | Singlet Excitation Energy (eV/molecule) |
|---|---|---|
| fumaronitrile | 186 | 4.68 |
| 1-cyanonaphthalene | 299 | 3.95 |
| naphthalene | 218 | 3.95 |
| tetramethyl-p-phenylene diamine | 260 | 3.41 |
| diethyl aniline | 217 | 3.84 |

When M and Q are properly selected, the wavelengths of the peak fluorescent emissions from M* and MQ* will be substantially different, and for purposes of this invention should be at least 50 nanometers apart. Typically these exciplexes will be strongly emitting and will have binding energies of about 14 Kcal/mole to about 35 Kcal/mole. In addition to selecting the proper M and Q to achieve adequate wavelength separation, it is possible to manipulate the concentrations of M and Q such that the vapor phase emission is predominantly from M* and the liquid phase emission is predominantly from MQ*.

$$M^* + Q = MQ^* \tag{1}$$

In the vapor phase, the densities are much lower and, one would expect, the potential for stabilization of the relatively polar exciplex (MQ*) is less; hence the equilibrium shifts toward the left in the equation, i.e. toward dissociation of the exciplex. Thus, in the vapor the fluorescence is dominated by the monomer (M*) emission. In these systems, M can range from about 0.001% to about 99.9% of the fluid system and Q can be the balance. Typically, however, M will be from about 2 to about 10% and Q will range from about 0.1 to about 1%.

A number of examples of candidate exciplex systems are listed in Table III. In Table III it should be noted that $\lambda max^M$ is the wavelength maxima at which the excited monomer fluoresces; $\lambda max^E$ is the wavelength maxima at which the excited exciplex fluoresces and $\Delta H$ is the binding energy of the exciplex.

TABLE III

Exciplex Systems

| Monomer | Quencher | λ max$^M$ (nm) | λ max$^E$ (nm) | ΔH (Kcal/mole) |
|---|---|---|---|---|
| naphthalene | tetramethyl-p-phenylene diamine | 340 | 470 | 14 |
| naphthalene | fumaronitrile | 340 | 440 | 20 |
| 1,2,4-trimethyl benzene | fumaronitrile | 288 | 430 | 27 |
| 1,2,3-trimethyl benzene | fumaronitrile | 288 | 406 | 23 |
| tetramethyl-p-phenylene diamine | 1-cyano-naphthalene | 340 | 618 | 26 |

One method for designing an exciplex probe system is based primarily on the correlations developed by A. Weller and D. Rehm, Zeit. Phys. Chem. (Frankfurt), Vol. 69, 183 (1970), who found that the exciplex binding energy and emission frequency are given by the following two equations $$\Delta H = \Delta' E_{o,o} - [E(D/D^+) - E(A^-/A)] - 0.13 \text{ eV} \tag{2}$$

and $$h\nu_c max = [E(D/D^+) - E(A^-/A)] - 0.15 \text{ eV} \tag{3}$$

where $\Delta H$ is the binding energy of the exciplex, $\Delta E_{oo}$ is the energy separation between the ground vibrational levels of the ground and first excited singlet electronic states of the monomer, $E(D/D^{*+})$ and $E(A^-/A)$ are the oxidation potential of the donor molecule, and the reduction potential of the acceptor molecule, measured in acetonitrile, respectively, and $h\nu_c max$ is the energy of the exciplex emission at the maximum of the exciplex emission intensity.

The equilibrium constant (K) for the exciplex formation is given by $$K = \frac{[MQ^+]}{[M^+][Q]} = \exp[-\Delta H - T\Delta S/RT] \tag{4}$$

where $\Delta S$ is found to be approximately $-20$ cal/K over a wide range of exciplexes, R. A. Caldwell and D. Creed, Acc. Chem. Res., Vol. 13, 45 (1981), [MG+] is the exciplex concentration, [M+] is the concentration of the excited monomer, and [Q] is the concentration of the quencher. In addition $\Delta H$ and $\Delta S$ are the respective ethalpy and entropy changes of the reaction; R is the gas constant and T is the absolute temperature. Consequently, use of the fluorescence spectra compiled by I. B. Berlman, *Handbook of Fluorescence Spectra of Aromatic Molecules*, Academic Press, New York, 1971, tables of oxidation and reduction potentials, *Technique of Electroorganic Synthesis*, Part II, Ed. by N. L. Weinberg, Vol. 5, in *Techniques of Chemistry*, Ed. by A. Weissberger, Wiley-Interscience, New York, 1975, p. 6-667 ff, and tables of boiling points, *Handbook of Chemistry and Physics*, 62nd Ed., CRC Press, Boca Raton, 1982, allows one to assess the probable usefulness of a wide variety of exciplex systems prior to testing.

The relative fluorescence yields of the exciplex ($\phi e$) and monomer ($\phi m$) are given by $$\frac{\phi e}{\phi m} = \frac{K_{fe}}{K_{fm}} \frac{[MQ^+]}{[M^+]} = \frac{K_{fe}}{K_{fm}} K[Q] \tag{5}$$

$K_{fe}$ for exciplexes is typically in the range of $10^6$–$10^7$ sec$^{-1}$, R. A. Caldwell and D. Creed, Acc. Chem Res., Vol. 13, 45 (1981), and $K_{fm}$ can be obtained from Berlman's compilation. Where $K_{fe}$ and $K_{fm}$ are the rate constant of the fluorescence for the exciplex and monomer respectively and [MQ+], [M+], are the concentrations of the exciplex and the excited monomer, K is the constant for the concentration of the quencher, [Q].

The fluid material to be studied may be fuel, typically jet fuel, gasoline or a synthetic derivative from coal or shale oil, or any other relatively volatile material which may be dispersed into a vapor-liquid and multiphase system. After M and Q are introduced, the fluid is made homogenous by mixing, stirring or any other conventional means.

The fluid is then dispersed into droplets and vaporized. Generally this is done by passing the fluid through a fuel spray nozzle, however, any system which disperses the liquid will do. Additionally, the liquid may be vaporized and studied without dispersion. Typically, the liquid is heated to aid in vaporization of the dispersed liquid. The monomer is then excited by directing a source of energy at it at the proper wavelength. The excited monomer $M^*$ then combines with the quencher (Q) to form the exciplex. This may be accomplished by any of the conventional techniques known to those skilled in the art. Typically, these consist of metal vapor lamps, high pressure arc lamps, laser beams, etc. The vapor and liquid phases and their spatial distribution is then determined by detecting, through use of appropriate optical filters, the fluorescence emitted by $M^*$ and $MQ^*$ which are present in one phase or the other. This detection may use any number of devices known to those skilled in the art, i.e. photographic film, photomultiplier tubes, diode arrays, etc. This technique has primary utility in the study of such two-phase systems qualitatively. However, it may be used to do quantitative studies as well.

EXAMPLE

A liquid/vapor visualization study of a synthetic diesel fuel was undertaken as follows using the present invention:

A synthetic diesel fuel was mixed comprising about 2.5% by weight naphthalene in cetane. The naphthalene served as the monomer M and the quencher Q was N,N,N',N'-tetramethyl-p-phenylene diamine (TMPD). The TMPD was added at the concentration of 1% by weight. The naphthalene was scintillation grade (99+%) and the TMPD was 98% purity both of which were Aldrich chemicals available from the Aldrich Chemical Company. The cetane was a practical grade (97%) from the Kodak Corporation.

In a series of demonstrations utilizing the system in FIG. 3, a fuel spray 2, approximately 1/6 gallon/hour, was generated with a simplex nozzle 4 and irradiated with a sheet of laser light 6. The resulting fluorescent emissions were then photographed by a camera 8 at right angles to the laser beam. Through use of the appropriate filters (not shown), the vapor and liquid emission patterns were separately photographed. With high speed film, adequate exposures could be obtained with a single laser shot, and since the laser pulse lasts only 10–20 nanoseconds and the fluorescence only 10–100 nanoseconds, these photographs represent frozen-flow results.

A neodymium yttrium, aluminum, garnet (Nd:YAG) laser 12, which is commercially available, was used to excite the monomer. The fourth harmonic of Nd:YAG at 266 nm 14 (approximately 80 mJ/pulse) was expanded in the vertical dimension through use of a cylindrical lens telescope (not shown) to a vertical dimension of approximately 40 mm. A final cylindrical lens 32 focuses the laser sheet to a thickness of 1–2 mm.

The simplex fuel spray nozzle 4 (Delavan hollow cone, 0.5 gph, 45° cone angle) was contained within a six arm glass cross 18 to confine the fuel vapor from the spray. The fuel tube 20 for the nozzle 2 enters through the upper flange 22 on the six inch primary arm 24 of the cross 18 and supports the nozzle 4 within the field of view 26. The nitrogen flow 28 also enters through the upper flange 22, passes over a coiled heating tape 30, through two inches of aluminum honeycomb (used as a flow straightener) not depicted, and past the nozzle 4. Below the spray visualization region 26, a six inch glass tee, not shown, provides a duct for the nitrogen/fuel vapor exhaust to be carried to the fume hood, not depicted. At the bottom of the tee, the liquid fuel is collected and reused in subsequent visualization experiments.

The laser sheet entered through two inch quartz windows, not depicted mounted on the cross 34. The photographs were taken through three inch quartz windows, not depicted, mounted on the cross 38, and through the optional filter 36.

Photographs were taken of the excited system with photographic color film. The monomer which predominates in the vapor phase fluoresced at about 380 nm and the exciplex which was predominant in the liquid, fluoresced at about 480 nm. A schematic of the system is shown in FIG. 1 which represents the chemical reactions which take place in this system and the fluorescent wavelengths of each excited species. Photographs of the system were taken using a Graphflex camera with a 38 mm lens and four inch by five inch sheet film. FIG. 4 is photographed without filters; FIG. 5 is photographed with the visible transmitting filter, Schott GG475, and gives the liquid only; FIG. 6 is photographed with the ultraviolet transmitting filter (Schott UG-11) and gives the vapor only. The Nd:YAG laser pulse has a width of approximately 10 nanoseconds full width half maximum (FWHM); the fluorescence lifetime of the exciplex is presently unknown, but typical exciplex lifetimes are on the order of 10–100 nanoseconds. Hence, these photographs, taken with Royal X Pan (ASA 1000) with a single laser shot, are frozen flow photographs, i.e. the motion of the particles in the spray is stopped because the effective shutter speed is 10–100 nanoseconds. In FIG. 4, the liquid sheet and the flow instabilities which lead to breakup of the sheet can be seen as well as the individual droplets. No particular significance should be assigned to the sizes of the small droplets since the precision of focus of the camera system can radically alter the perceived photographic size. The gray interior of the spray is predominantly vapor. In FIG. 6, the vapor pattern is shown; as before the vapor pattern lies within the spray cone, but now there are apparent lighter and darker areas within the vapor region. There are apparently temporal and spatial inhomogeneities in the evaporation of the spray.

The present method allows for the in situ observation of the spatial and phase distribution of a liquid-vapor multiphase fluid system. Such observations offer an opportunity for a better understanding of the dynamics of the individual phases during their conversion and distribution. The improved understanding will in turn give the designers of components or systems which utilize such fluids, the information they require to optimize their designs and improve their systems.

Examples of industries which have a need for this information are the automobile industry and the aerospace engine industry. Both of these industries are concerned with the combustion of a liquid-vapor fluid system. A great deal of time and money is spent on research in this area trying to improve techniques for getting better dispersion, phase distribution, fuel and oxidant mixture, etc. to improve engine efficiency and power. Much of the effort is involved in designing fuel injection or combustors to achieve this improvement.

The present method can supply the information concerning these designs quickly and accurately.

Other industries which may find this method helpful are the paint manufacturers and ink manufacturers. Their primary concern would be in developing proper techniques and fluid systems which would improve their spray application or jet application systems. Another industry which may find this method helpful is the steam boiler industry.

It should be understood that the invention is not limited to the particular embodiments shown and described herein but that various changes and modifications may be made without departing from the spirit and scope of this novel concept as defined by the following claims.

I claim:

1. A method for determining the spatial and phase distribution of a liquid-vapor multiphase fluid comprising:

adding a fluorescent monomer and a quencher to a fluid, dispersing the fluid to produce a liquid-vapor multiphase fluid, exciting the monomer by directing an energy source of a proper wavelength at the dispersed fluid, the excited monomer then combines with the quencher to produce a fluorescent exciplex in the dispersed fluid, determining the spatial and phase distribution of the dispersed fluid by detecting the relative fluorescence of both the fluorescent monomer and exciplex in the dispersed fluid, said fluorescent monomer being present primarily in the vapor phase and said fluorescent exciplex being present primarily in the liquid phase.

2. The method of claim 1 wherein the fluid is dispersed by passing it through a fuel spray nozzle.

3. The method of claim 1 wherein the monomer is naphthalene and the quencher is tetramethyl-p-phenylene diamine.

4. The method of claim 1 wherein the monomer is excited by subjecting the dispersed fluid to laser radiation.

* * * * *